United States Patent [19]

Kampmann et al.

[11] Patent Number: 5,374,728

[45] Date of Patent: Dec. 20, 1994

[54] PROCESS FOR THE PREPARATION OF 2-AMINOMETHYLPIPERIDINE

[75] Inventors: Detlef Kampmann, Bochum; Gregor Deckers, Xanten; Claus Kniep, Oberhausen, all of Germany

[73] Assignee: Hoechst Aktiengesellschaft, Germany

[21] Appl. No.: 950,431

[22] Filed: Sep. 23, 1992

[30] Foreign Application Priority Data

Oct. 2, 1991 [DE] Germany .................... 4132808

[51] Int. Cl.⁵ .................................. C07D 211/02
[52] U.S. Cl. ......................................... 546/185
[58] Field of Search .................................... 546/185

[56] References Cited

U.S. PATENT DOCUMENTS

| | | | |
|---|---|---|---|
| 2,507,631 | 5/1950 | Hartmann et al. | 546/185 |
| 3,246,000 | 4/1966 | Baizer | 260/295.5 |
| 3,717,593 | 2/1973 | Zondler et al. | 546/185 |
| 3,890,329 | 6/1975 | Benezra | 546/185 |

FOREIGN PATENT DOCUMENTS 1530809  6/1966  France .

OTHER PUBLICATIONS

Chemical Abstracts, vol. 106, 1987, Abstract #176178K JPA-86-251,663 ; Nov. 8, 1986.

*Primary Examiner*—C. Warren Ivy
*Assistant Examiner*—Raymond Covington
*Attorney, Agent, or Firm*—Jordan B. Bierman

[57] ABSTRACT

A process for the preparation of 2-aminomethylpiperidine by catalytic hydrogenation of 2-cyanopyridine in the presence of a cobalt-containing catalyst at elevated temperature and under elevated pressure. The reaction can be carried out either in two steps or in a single stage.

21 Claims, No Drawings

PROCESS FOR THE PREPARATION OF 2-AMINOMETHYLPIPERIDINE

The present invention relates to a process for the preparation of 2-aminomethylpiperidine by the catalytic hydrogenation of 2-cyanopyridine.

The process follows the equation

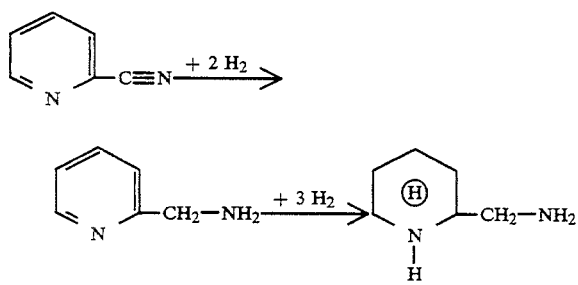

BACKGROUND OF THE INVENTION

The reaction proceeds in the presence of a suitable catalyst under pressure and at elevated temperature, 2-aminomethylpyridine initially being formed as an intermediate in the first step. The desired 2-aminomethyl piperidine is formed from the 2-aminomethylpyridine in a subsequent second hydrogenation step.

European patent 189,678 relates to the electrochemical reduction of 2-cyanopyridine to 2-aminomethylpyridine; it follows from U.S. Pat. Nos. 4,153,605 and 4,080,338 that the hydrogenation of 2-cyanopyridine by means of palladium/activated charcoal catalysts leads predominantly to α-bispicolylamine. 2-Aminomethyl piperidine, on the other hand, is formed only in minor amounts.

The conversion of 2-aminomethylpyridine to 2-aminomethylpiperidine by means of $PtO_2$ catalysts in aqueous solution acidified with acetic acid is described in U.S. Pat. Nos. 3,772,230 and 3,631,046. However, the final working-up required—liberation of the amine with potassium hydroxide, extraction with diethyl ether, drying of the ether phase over sodium sulfate and fractional distillation—is very expensive.

Another process for the preparation of 2-aminomethylpiperidine forms the subject matter of Japanese Patents 86/251 663 and 86/251 659. According to the former, a solution of 2-cyanopyridine in benzene, with ammonia added, is hydrogenated to 2-aminomethylpyridine by means of Raney nickel. In a separate step, according to the latter reference, 2-aminomethylpyridine is converted to 2-aminomethylpiperidine with hydrogen in the aqueous phase in the presence of rhodium/activated charcoal as a catalyst. Because of the use of two different catalysts and the need to work in two different media—benzene solution on the one hand and aqueous phase on the other—the combined process is very laborious and impractical. Moreover, the final separation of the 2-aminomethylpiperidine from the aqueous solution formed involves considerable expense.

There is, therefore, a need for a process which avoids the disadvantages of the above-mentioned processes and which provides a method of hydrogenating 2-cyanopyridine to 2-aminomethylpiperidine using one and the same catalyst and without changing the solvent. The process should use a catalyst which is available in commercial quantities and should be able to be carried out at justifiable expense, even on an industrial scale. Furthermore, there should be the assurance that the reaction does not result in the formation of substantial amounts of by-products, but produces the desired useful product, namely 2-aminomethylpiperidine, in good yield.

DESCRIPTION OF THE INVENTION

These objects are achieved by a process for the preparation of 2-aminomethylpiperidine which comprises reacting 2-cyanopyridine with hydrogen in the presence of a cobalt-containing catalyst at 120° to 230° C. and 10 to 45 MPa.

Useful cobalt-containing catalysts are conventional, commercially available, cobalt which can be supplied in industrial quantities. When choosing suitable cobalt catalysts, care should be taken to ensure that the catalyst contains a sufficient amount of cobalt. In general the proportion of cobalt should be 25% to 85%, preferably 30% to 75%, and most preferably 40% to 60% by weight of cobalt, based on the total weight of catalyst.

In addition to cobalt, the catalysts may also contain activators and promoters. Suitable activators are Zr, Mn, Cr, and V, especially Zr, Mn and Cr, and most preferably Zr and Mn. Useful promoters are alkali metals and alkaline earth metals, especially one or more of Li, Na, K, Mg, Ca, and Ba, preferably Na, K, Mg, and Ca. The catalyst contains both the activators and the promoters in conventional amounts. Their combined proportion is 2.5% to 40%, especially 5% to 35%, and most preferably 10% to 30% by weight, based on the total weight of catalyst.

It is particularly advantageous to use supported catalysts as the cobalt-containing catalysts. Such supported catalysts can be prepared by known methods, for example by precipitation and by impregnation. Supports which can be used include alumina, activated charcoal, silicates, silica gel, kieselguhr; especially Ca, Mg, or Al silicates, silica gel, and kieselguhr, preferably silica gel and kieselguhr, and most preferably kieselguhr. The cobalt-containing catalyst comprises 15% to 65%, especially 20% to 60%, and most preferably 20% to 50% by weight of support, based on the total weight of catalyst.

The cobalt-containing catalyst can be used either in stabilized form or as a pyrophoric product. Because it is easier to handle, a stabilized catalyst, i.e. a catalyst which has been rendered inert to the action of air, is frequently preferred. It has been shown, however, that pyrophoric cobalt-containing catalysts usually give better results than corresponding stabilized catalysts. Pyrophoric cobalt catalysts are particularly recommended for this reason.

A further advantage of the process according to the invention is that it is particularly flexible; it is not restricted exclusively to a two-stage process, in which 2-cyanopyridine is first hydrogenated to 2-aminomethylpyridine and the latter is then hydrogenated to 2-aminomethylpiperidine, but can be applied quite easily as a one-stage reaction. This one-stage process variant complies particularly well with the demands made on an industrial process, because it can be carried out much more easily than a two-stage process and additionally affords an appreciable reduction in the cost of equipment.

Independently of a two-stage or one-stage embodiment, the process according to the invention can be carried out either batchwise—for example in a pressure-resistant vessel equipped with a stirrer or an autoclave—or continuously. It is particularly suitable for continuous operation.

In a continuous operation, it is conventional to use pressure-resistant tube reactors in which the cobalt-containing catalyst is arranged in lumps as a fixed bed. The starting materials, i.e. 2-cyanopyridine and hydrogen, are introduced into the tube reactor either at the top or at the bottom, the procedures accordingly being referred to as trickle or bottom procedures, respectively. Depending on how the starting materials are introduced, the reaction mixture leaves the tube reactor either at the bottom or at the top. The reaction can be carried out either in a straight pass or with reaction product circulation.

In one particular embodiment, the starting materials are introduced into the tube reactor at the bottom and the reaction takes place in a straight pass, i.e. without any part of the reaction product being circulated. The reaction mixture leaves the tube reactor at the top.

On the one hand the reaction conditions, especially pressure and temperature, are dependent on whether the process is carried out in two stages or one stage, and on the other hand they are also influenced to a certain extent by the type of cobalt-containing catalyst and accordingly have to be matched with one another.

If a two-stage process is chosen, the reaction is carried out in the first stage at 120° C. to 160°, preferably 130° C. to 150° C., and most preferably 135° C. to 145° C., and at 10 to 20 MPa, especially 10 to 15 MPa. In the second stage, the temperatures are 160° C. to 230° C., especially 170° C. to 200° C., and most preferably 175° C. to 190° C., and at 20 to 45 MPa, especially 25 to 40 MPa, and preferably 25 to 35 MPa. If a one-stage process is used, the reaction is carried out in a single stage at temperatures of 160° C. to 230° C., especially 170° C. to 200°, and preferably 175° C. to 195° C. and at pressures of 20 to 45 MPa, especially 25 to 40 MPa, and most preferably 25 to 35 MPa.

To have a favorable effect on the hydrogenation, hydrogen is used in excess of the stoichiometric requirement. Unconsumed hydrogen is separated out of the reaction product leaving the reactor, for example by means of a high-pressure gas separator and a downstream low-pressure gas separator, and reintroduced into the reaction, if necessary after compression.

To suppress reactions which lead to the elimination of ammonia, the process can be operated in the presence of ammonia, which is added to the hydrogen gas, if required. It has been found, however, that it is possible to dispense with the addition of ammonia in the majority of cases, without impairing the conversion.

2-Cyanopyridine is a solid with a melting point of about 28° to 30° C. To handle 2-cyanopyridine more easily, it is advisable to use a solvent. 0.5 to 5, particularly 1.0 to 3.0, and most preferably 1.5 to 2.5 parts by weight of solvent are used per part by weight of 2-cyanopyridine. The solvent should be essentially inert to the reaction, i.e. it should be insusceptible or only slightly susceptible to hydrogenation and should not undergo any reaction with the starting material or the reaction mixture formed. Suitable solvents include tetrahydrofuran, dioxane, toluene, xylene, and cumene, especially tetrahydrofuran, dioxane, and toluene, and most preferably toluene. It is also possible to use mixtures of the above-mentioned solvents. To isolate 2-aminomethylpiperidine, the reaction mixture is subjected to fractional distillation after the separation of gaseous constituents, for example hydrogen and/or ammonia.

2-Aminomethylpiperidine is used as an intermediate for the production of pharmaceuticals.

The Examples described below illustrate the present invention without limiting it.

COMPARATIVE EXPERIMENTS

Comparative Experiment 1 a)

Preparation of 2-aminomethylpyridine 52 g of cyanopyridine, 260 g of toluene, and 5 g of a nickel catalyst containing about 50% to 53% by weight of Ni and 25% to 30% by weight of kieselguhr as the support are placed in an autoclave (volume 1 liter) equipped with a lifting stirrer.

65 g of $NH_3$ (corresponding to 7.6 mols of $NH_3$ per mol of cyanopyridine) are then added and hydrogen is introduced under pressure until an initial pressure of 3.0 MPa is attained. The autoclave is heated, with stirring, and the pressure required for carrying out the reaction is kept constant by the addition of hydrogen.

| Reaction conditions: | |
|---|---|
| Pressure | 10 MPa |
| Temperature | 120° C. |
| Reaction time | 3 hours |

When the reaction is complete, the reaction mixture is freed of excess $NH_3$ and hydrogen, and separated from the catalyst by filtration.

Comparative Experiment 1 b)

Preparation of 2-aminomethylpiperidine 116 g of the reaction mixture resulting from Comparative Experiment 1 a) and 2 g of a rhodium catalyst (4.83% by weight of Rh on activated charcoal as a support) are placed in an autoclave (volume 0.25 liters) equipped with a lifting stirrer. Hydrogen is then introduced under pressure until an initial pressure of 2.0 MPa is attained. The autoclave is heated, with stirring, and the pressure required for carrying out the reaction is kept constant by the addition of hydrogen.

| Reaction conditions: | |
|---|---|
| Pressure | 4 MPa |
| Temperature | 110° C. |
| Reaction time | 2 hours |

Comparative Experiment 1 c)

Preparation of 2-aminomethylpiperidine according to U.S. Pat. No. 3,772,230

48.2 g of the reaction mixture resulting from Comparative Experiment 1 a), 86 g of acetic acid, and 5 g of a platinum catalyst (about 5% by weight of Pt on an activated charcoal support) are placed in an autoclave (volume 0.25 liters) equipped with a lifting stirrer. Hydrogen is then introduced under pressure until an initial pressure of 0.2 MPa is attained. The autoclave is heated, with stirring, and the pressure required for carrying out the reaction is kept constant by the addition of hydrogen.

| Reaction conditions: | |
|---|---|
| Pressure | 0.35 MPa |
| Temperature | 50° C. |
| Reaction time | 5 hours |

Comparative Experiment 2

Preparation of 2-aminomethylpyridine 208 g of cyanopyridine, 208 g of toluene, and 20.8 g of Raney Ni are placed in an autoclave (volume 1 liter) equipped with a lifting stirrer. 340 g of $NH_3$ (corresponding to 10 mol of $NH_3$ per mol of cyanopyridine) is then added and hydrogen is introduced under pressure until an initial pressure of 3.0 MPa is attained. The autoclave is heated, with stirring, and the pressure required for carrying out the reaction is kept constant by the addition of hydrogen.

| Reaction conditions: | |
|---|---|
| Pressure | 10 MPa |
| Temperature | 90° C. |
| Reaction time | 4 hours |

When the reaction is complete, the reaction mixture is freed of excess $NH_3$ and hydrogen and separated from the catalyst by filtration.

EXAMPLES

Example 1 a)

Two-stage Preparation of 2-aminomethylpyridine 416 g of cyanopyridine, 832 g of toluene, and 83.2 g of a pyrophoric cobalt catalyst containing about 44% to 47% by weight of Co and 25% to 30% by weight of kieselguhr as the support are placed in an autoclave (volume 5 liters) equipped with a lifting stirrer. The addition of $NH_3$ is omitted. Hydrogen is introduced under pressure, the autoclave is heated, with stirring, and the pressure required for carrying out the reaction is kept constant by the addition of hydrogen.

| Reaction conditions | |
|---|---|
| Pressure | 10 MPa |
| Temperature | 140° C. |
| Reaction time | 50 min |

When the reaction is complete, the reaction mixture is freed of excess hydrogen and separated from the catalyst by filtration.

Example 1 b)

Preparation of 2-aminomethylpiperidine 72 g of the reaction mixture resulting from Example 1 a) and 5.2 g of a stabilized cobalt catalyst containing about 44% to 47% by weight of Co and 25% to 30% by weight of kieselguhr as the support are placed in an autoclave (volume 0.25 liters) equipped with a lifting stirrer. The addition of $NH_3$ is omitted. Hydrogen is introduced under pressure, the autoclave is heated, with stirring, and the pressure required for carrying out the reaction is kept constant by the addition of hydrogen.

| Reaction conditions: | |
|---|---|
| Pressure | 25 MPa |
| Temperature | 180° C. |
| Reaction time | 8 h 40 min |

Example 2

One-stage Preparation of 2-aminomethylpiperidine 26 g of cyanopyridine, 52 g of toluene, and 5.1 g of a pyrophoric cobalt catalyst containing about 44% to 47% by weight of Co and 25% to 30% by weight of kieselguhr as the support, as mentioned in Example 1 a), are placed in an autoclave (volume 0.25 liter) equipped with a lifting stirrer. The addition of $NH_3$ omitted. Hydrogen is introduced under pressure, the autoclave is heated, with stirring, and the pressure required for carrying out the reaction is kept constant by the addition of hydrogen.

| Reaction conditions: | |
|---|---|
| Pressure | 25 MPa |
| Temperature | 180° C. |
| Reaction time | 3.5 hours |

Example 3

One-stage Preparation of 2-aminomethylpiperidine 624 g of cyanopyridine, 1248 g of toluene, and 125.6 g of a pyrophoric cobalt catalyst containing about 44% to 47% by weight of Co and 25% to 30% by weight of kieselguhr as the support, as mentioned in Example 1 a), are placed in an autoclave (volume 5 liters) equipped with a lifting stirrer. The addition of $NH_3$ is omitted. Hydrogen is introduced under pressure, the autoclave is heated, with stirring, and the pressure required for carrying out the reaction is kept constant by the addition of hydrogen.

| Reaction conditions: | |
|---|---|
| Pressure | 25 MPa |
| Temperature | 180° C. |
| Reaction time | 3 h 40 min |

The results of the Comparative Experiments and the Examples are collated in the Table below.

TABLE

| Composition[1] | Comparative Experiment | | | | Example | | | |
|---|---|---|---|---|---|---|---|---|
| | 1a | 1b | 1c | 2 | 1a | 1b | 2 | 3 |
| First runnings | 2.2 | — | 0.4 | 0.5 | 4.6 | 32.2 | 30.9 | 26.8 |
| 2-Aminomethylpiperidine | — | 14.4 | 6.2 | <0.01 | — | 57.0 | 60.1 | 61.6 |
| Component | — | — | — | 0.3 | — | — | — | <0.1 |
| 2-Aminomethylpyridine | 76.8 | 40.5 | 51.5 | 62.0 | 88.4 | 1.5 | 0.3 | 0.6 |
| 2-Cyanopyridine | — | — | — | 23.1 | — | — | 0.2 | — |
| Higher-boiling fractions | 21.0 | 45.1 | 41.9 | 14.1 | 7.0 | 9.3 | 8.5 | 10.9 |
| Conversion[2] (%) | 100.0 | 100.0 | 100.0 | 76.9 | 100.0 | 100.0 | 99.8 | 100.0 |
| Selectivity* (%) | 76.8 | 40.5 | 51.5 | 80.6 | 88.5 | 1.5 | 0.3 | 0.6 |

TABLE-continued

| Composition[1] | Comparative Experiment | | | | Example | | | |
|---|---|---|---|---|---|---|---|---|
| | 1a | 1b | 1c | 2 | 1a | 1b | 2 | 3 |
| Selectivity** (%) | — | 14.4 | 6.2 | — | — | 57.0 | 60.3 | 61.6 |
| Yield[3] (%) | 76.8 | — | — | 62.0 | 88.5 | 1.5 | 0.3 | 0.6 |
| Yield[4] (%) | — | 14.4 | 6.2 | — | — | 57.0 | 60.1 | 61.6 |

[1] gas chromatographic analysis in % by weight without solvent and ammonia
[2] based on 2-cyanopyridine
[3] 2-aminomethylpyridine based on 2-cyanopyridine
[4] 2-aminomethylpiperidine based on 2-cyanopyridine
*formation of 2-aminomethylpyridine
**formation of 2-aminomethylpiperidine While only a limited number of specific embodiments of the present invention have been expressly disclosed, it is, nonetheless, to be broadly construed, and not to be limited except by the character of the claims appended hereto.

What we claim is:

1. A process for the preparation of 2-aminomethyl piperidine by a reaction which is a catalytic hydrogenation of 2-cyano pyridine, comprising reacting 2-cyanopyridine with hydrogen in the presence of a cobalt-containing catalyst at a reaction temperature of 120° C. to 230° C. and a reaction pressure of 10 to 45 MPa.

2. The process of claim 1 wherein said catalyst contains at least 25% to 85% by weight of cobalt.

3. The process of claim 2 wherein said catalyst contains 30% to 75% by weight of cobalt.

4. The process of claim 3 wherein said catalyst contains 40% to 60% by weight of cobalt.

5. The process of claim 1 wherein said catalyst contains a support.

6. The process of claim 1 wherein said catalyst contains at least one support selected from the group consisting of alumina, activated charcoal, silicates, silica gel, and kieselguhr.

7. The process of claim 6 wherein said support is selected from the group consisting of silicates, silica gel, and kieselguhr.

8. The process of claim 7 wherein said support is kieselguhr.

9. The process of claim 1 wherein said catalyst contains 5% to 60% by weight of said support.

10. The process of claim 9 wherein said catalyst contains 10% to 50% by weight of said support.

11. The process of claim 10 wherein said catalyst contains 15% to 50% by weight of said support.

12. The process of claim 1 wherein there is a first stage and a second stage, said 2-cyano pyridine being converted to 2-aminomethyl pyridine in said first stage, said 2-aminomethyl pyridine being converted to said aminomethyl piperidine in said second stage, said first stage being carried out at a first temperature of 120° C. to 160° C. and at a first pressure of 10 to 20 MPa, said second stage being carried out at a second temperature of 160° C. to 230° C. and at a second pressure of 20 to 45 MPa.

13. The process of claim 12 wherein said first temperature is 130° C. to 150° and said second temperature is 170° to 200° C.

14. The process of claim 13 wherein said first temperature is 135° C. to 145° C. said first pressure is 10 to 15 MPa, said second temperature is 175° C. to 190° C. and said second pressure is 25 to 35 MPa.

15. The process of claim 1 wherein there is a single stage, said single stage being carried out at a reaction temperature of 160° C. to 230° C. and a reaction pressure of 20 to 45 MPa.

16. The process of claim 15 wherein said reaction temperature is 170° C. to 200° C. and said reaction pressure is 25 to 40 MPa.

17. The process of claim 16 wherein said reaction temperature is 175° C. to 190° C. and said reaction pressure is 25 to 35 MPa.

18. The process of claim 1 wherein a solvent is present, said solvent being substantially inert to said reaction.

19. The process of claim 1 wherein said solvent is selected from the class consisting of tetrahydrofuran, dioxane, toluene, xylene, cumene, and mixtures thereof.

20. The process of claim 19 wherein said solvent is selected from the group consisting of tetrahydrofuran, dioxane, toluene, and mixtures thereof.

21. The process of claim 20 wherein said solvent is toluene.

* * * * *